United States Patent
Meller et al.

(10) Patent No.: US 6,214,626 B1
(45) Date of Patent: *Apr. 10, 2001

(54) APPARATUS (CUVETTE) FOR TAKING UP AND STORING LIQUIDS AND FOR CARRYING OUT OPTICAL MEASUREMENTS

(75) Inventors: Paul Meller, Marburg; Jürgen Gross, Hofheim, both of (DE)

(73) Assignee: Dade Behring Marburg GmbH, Marburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/993,317

(22) Filed: Dec. 18, 1997

(30) Foreign Application Priority Data

Dec. 19, 1996 (DE) .................................. 196 52 784

(51) Int. Cl.[7] ...................................... G01N 1/14
(52) U.S. Cl. .................. 436/165; 436/180; 422/100; 422/102; 356/246
(58) Field of Search .................. 422/100, 102; 356/246; 73/863.71, 864.02; 436/164, 165, 180

(56) References Cited

U.S. PATENT DOCUMENTS

| 4,420,254 | 12/1983 | Smeaton | 356/246 |
|---|---|---|---|
| 5,260,030 | 11/1993 | DeVaughn . | |
| 5,393,494 | * 2/1995 | Greenfield et al. | 422/68.1 |
| 5,525,518 | * 6/1996 | Lundsgaard et al. | 436/68 |
| 5,844,686 | 12/1998 | Treptow et al. | 356/440 |
| 5,846,492 | * 12/1998 | Jacobs et al. | 422/67 |

FOREIGN PATENT DOCUMENTS

| 30 29 718 A1 | 8/1980 | (DE) . |
|---|---|---|
| 195 35 046 A1 | 9/1995 | (DE) . |
| 0 701 865 A1 | 3/1996 | (EP) . |

* cited by examiner

Primary Examiner—Jeffrey Snay
(74) Attorney, Agent, or Firm—Finnegan, Henderson, Farabow, Garret and Dunner, L.L.P.

(57) ABSTRACT

An apparatus which permits simultaneous use as reaction vessel for taking up one or more reaction liquids, for incubating and storing these liquids and for carrying out optical measurements is described. The apparatus performs functions of the reaction vessel and functions of the apparatus for liquid uptake. This makes it possible for analysis to be completely free of carryover while, at the same time, requiring minimal use of consumable materials or rinsing solutions.

21 Claims, 1 Drawing Sheet

APPARATUS (CUVETTE) FOR TAKING UP AND STORING LIQUIDS AND FOR CARRYING OUT OPTICAL MEASUREMENTS

BACKGROUND OF THE INVENTION

1. Field of the Invention

The present invention relates to an apparatus (cuvette) for taking up and storing liquids and for carrying out optical measurements 2. Description of the Background of the Invention In vitro diagnostic methods are increasingly characterized by automation of the tests and measurement procedures to be carried out. The background to this requirement comprises, on the one hand, the desire to exclude individual factors in the manipulation and carrying out by any operating staff and, on the other hand, the increasingly high costs associated with use of staff.

The development and carrying out of chemical methods of protein measurement in automated laboratory operation thus make great demands on the knowledge of the technical procedure and quality assurance.

The growing demands on the specificity and sensitivity of the tests and the simultaneous requirement for greater output by an analyzer therefore make it necessary to extend previous concepts of the manipulation of liquids. To carry out a chemical test for proteins, as a rule two types of liquid starting components are required: the sample obtained from the patient to be investigated, and the reagent components necessary for the diagnostic result.

While the sample comprises, after any necessary preparative steps (centrifugation, removal of cellular constituents or the like) have been carried out, only one component, the reagent is frequently composed of several constituents.

In the technical procedure for a diagnostic test, the sample and the test components must frequently be taken up in a particular sequence. With most analyzers, this is effected by a pipetting apparatus which carries out these steps successively or else combined in a suitable way. Between the individual tests, the parts of the pipetting apparatus coming into contact with the liquid, such as the inside and outside of the needle, are washed by a suitable cleaning solution so that they are available again without contaminated portions to take up the following sample or test liquids. Similar processes are carried out to clean reusable reaction vessels.

This process described above is thus suitable for continuous and automatic operation as long as the requirements for the cleaning conditions and the quality of the cleaning process are sufficiently consistent such that there are no measurable effects on a subsequent test due to constituents which may be bound by adsorption to the surface, or they can be precluded by other quality assurance measures in the test.

Unfortunately, many of the more recent diagnostic tests, such as the range of tumor markers or microbiological tests, now have no firmly defined diagnostically relevant region of measurement. In the case of tumor markers, it is necessary to determine all values above a particular threshold, and in microbiology it is necessary to be able to measure down to the region of a few molecules.

These requirements, therefore, frequently no longer permit the components coming into contact with the liquids to be cleaned by repeated washing without additional measures. In addition, traces of constituents of the cleaning solution remaining on the surface might themselves lead to irreversible falsification of the result. On the other hand, as the requirements increase there is a very large increase in the consumption of and thus the costs of cleaning solution. Measures to improve the cleaning, while at the same time reducing consumption require additional apparatus measures (heating the cleaning solution, source of ultrasound or the like).

In order to avoid all these difficulties, many suppliers of diagnostic analytical systems therefore already offer disposable articles for pipette tips and for reaction vessels. Another approach is to use ready-packaged test modules. In this case, the necessary constituents of the reagent are prepared so that it is now necessary only to add a sample and mix the reagent components.

The disadvantage of the last-mentioned process is the provision of the test components for the individual test, their preservation and storage inside and outside the analyzer. These measures can usually be implemented only at considerably more cost than removal of the test liquid from larger storage bottles. The technical procedure for tests in an analyzer usually entails separate transfer of liquids and provision of reaction vessels. In this case, the liquids are transferred by metering systems, which are coupled to movable units (X-Y-Z transfer arms), to the location of the reaction vessel when, possibly after further incubation steps, the reaction fluid present in the vessel is measured.

Thus, prior art analyzers involve use both of disposable articles for the metering in the form of exchangeable tips and of disposable articles as reaction vessels which are fed on demand continuously to a processing unit.

This procedure makes it possible to carry out measurements completely without carryover, it being necessary to use at least one exchangeable tip and one reaction vessel per analytical result. This results in a considerable contribution to the overall cost by consumables, which may be of the order of DM 0.05–0.30 per consumable article in the case of disposable articles suitable for automated equipment. In addition, the individual consumable articles must be processed inside the automatic analyzer. The taking up of the exchangeable tip, the liquid transfer and the discarding of the used tip on the one hand, and the feeding of disposable reaction vessels mean that a large number of electromechanical actuation units are required. The entire technical procedure is thus very time consuming. This has direct effects on the speed and the output of an automatic analyzer.

SUMMARY OF THE INVENTION

The object of the invention was thus, in order to overcome the disadvantages described with the requirements mentioned, and in order to make simpler technical operation possible by combining several process steps and achieve less costly use of material, to develop a novel reaction vessel which permits at the same time simultaneously the taking up of liquids, the storage of the test components and the carrying out of optical measurements. The object has been achieved according to the present invention by constructing a reaction vessel with an additional apparatus for taking up liquids, it being possible at the same time for the apparatus to be processed in the same manner as an exchangeable tip inside the analyzer.

The reaction vessel must, in order to be amenable to optical measurements, consist of a light-transmitting material such as, for example, poly(methyl methacrylate), polypropylene or the like.

Used for taking up the liquid components is an inlet channel which is attached to the underside of the reaction vessel and is in the form of an extended tube, having a diameter complying with the requirements for the precision of the removed volumes of liquid and a pointed profile. In order to ensure, when the liquid is taken up, that the liquid remains inside the reaction vessel, the top opening of the inlet apparatus is located above the base of the reaction vessel part which is designed as cuvette. This makes it possible, in a simple manner, by applying a reduced pressure, for volumes to be taken up from storage bottles and delivered completely into the cuvette. It is possible at the same time for any remaining residues of liquid to be delivered by applying a gas pressure. The achievable precision of liquid uptake is comparable to the precision achievable with commercially available exchangeable tips and is a few percent with volumes of 1–10 microliters. It is furthermore possible for the outside of the tip to be rinsed by conventional washing stations.

All the parts relating to the reaction vessel and required for carrying out optical measurements must likewise consist of a light-transmitting material in order to ensure optical transmission. The reaction vessel itself can be designed in a round, rectangular or polygonal shape, which is determined by the manufacturing and process requirements. In order to maximize heat transfer in any incubation steps, the walls should be as smooth as possible. To adapt the apparatus for use in optical methods, the walls of the reaction vessel can be flat or curved in a suitable manner to achieve an appropriate optical beam profile.

In addition to the requirements for the reaction vessel, the apparatus for liquid uptake must comply with other requirements: besides the geometrical requirements for the shape and the diameter of the pipette tip, the material should be suitable at the same time for recognizing the surface of a liquid. This can be achieved by using graphite-containing plastic material having conductive properties. It would likewise be possible alternatively to use steel needles as employed with many disposable medical articles.

The upper side of the reaction vessel has an opening for taking up the apparatus. This has the advantage that the apparatus can be taken up and discarded in the same manner as an exchangeable tip, and no additional mechanical actuation units are required. Addition of other liquids such as, for example, a buffer, is possible through a dilutor system which is connected to the exchangeable tip unit.

BRIEF DESCRIPTION OF THE DRAWINGS

Examples of embodiments of the invention are described below by means of the appended drawings.

DETAILED DESCRIPTION OF THE PREFERRED EMBODIMENTS

The cuvettes depicted in the appended figures consist of a light-transmitting plastic element 2, made for example of a poly(methyl methacrylate) injection molding. The shape of the element 2 can vary according to the described invention. It is likewise possible for the element 2 to be produced from various materials. An apparatus for taking up the liquid 4 is attached in the form of a pipette tip or in the form of a thin tube in the center or on the side of this element 2. Between an upper outlet of the liquid aspiring device and a bottom of the cuvette portion of the reaction vessel, a volume is defined. The volume is at least the volume of the liquid to be stored, and is between 50–500 $\mu$l. The material of this part can moreover be of a different material, for example of a conductive graphite-containing plastic or metal. Alternatively, it may be coated in parts with suitable conductive materials.

Figure 1:
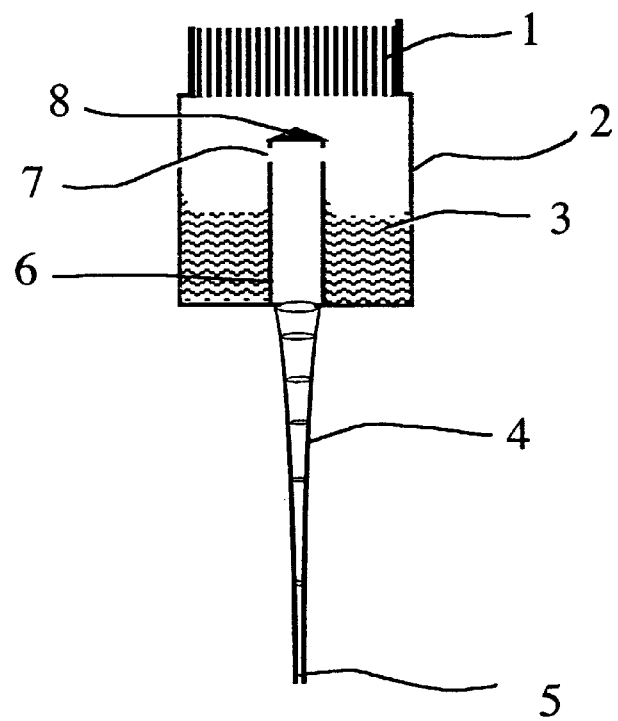
FIG. 1 shows a side view of a cuvette according to the invention with apparatus integrated in the center for liquid uptake.
Figure 2:
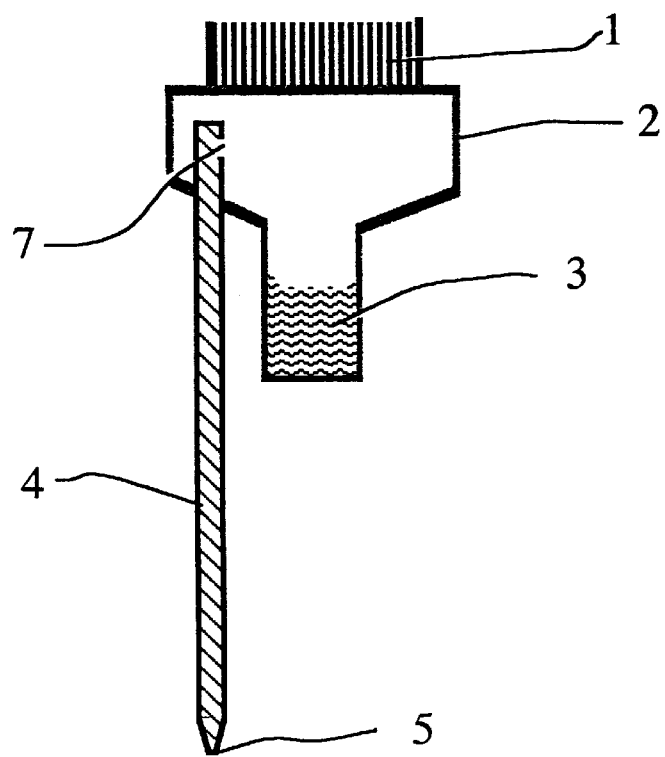
FIG. 2 shows a side view of a cuvette according to the invention with apparatus attached on the side for liquid uptake.

Whereas in FIG. 1 the pipette tip continues into the light-transmitting element 2 in the form of an overflow tube 6, the apparatus for taking up liquid 4 is attached on the side in the embodiment shown in FIG. 2. At the upper end of the filling apparatus 4 in each case there is an opening 7 for delivering the liquid 3 which has been taken up. The shape, edge thickness and diameter of the tip (5) are adapted to the requirements of metering precision.

Both embodiments comprise a holder 1 which permits the taking up, the transport and the delivery of the cuvettes in the same manner as exchangeable tips. For adding liquids through a connected dilutor system, the channels for liquid inlet and outlet can be separated by a suitable design of the overflow tube 8.

What is claimed is:

1. An apparatus for taking up, transporting and storing a liquid and for carrying out optical measurements, comprising:

a reaction vessel having a body which enables the storage of the liquid, the body being formed by walls, at least two walls being sufficiently transparent to permit light transmission for optical testing, a base portion of the reaction vessel forming a cuvette portion;

a liquid aspirating device extending into the body of the reaction vessel to such an extent that between an upper outlet of the liquid aspiring device and a bottom of the cuvette portion a volume is defined, which is at least the volume of the liquid to be stored; and a connecting device for connecting the reaction vessel to an exchangeable tip unit, the connecting device being located on an upper side of the reaction vessel.

2. The apparatus of claim 1, wherein the connecting device is configured for connecting to a dilutor system for feeding liquid into the cuvette portion.

3. The apparatus of claim 1, wherein the liquid aspirating device includes a tip of suitable length, edge thickness, and diameter for taking up liquids.

4. The apparatus of claim 1, wherein the connecting device is configured to be connected to a dilutor system suitable for using exchangeable tips.

5. The apparatus of claim 1, wherein the cuvette portion of the reaction vessel is configured to be processed as an exchangeable tip.

6. The apparatus of claim 1, wherein the reaction vessel with the attached liquid aspirating device is composed of at least one of different conductive or non-conducting plastic materials, composite materials, and combinations of plastic and metal.

7. The apparatus of claim 1, wherein the cuvette portion is at least partially coated with at least one conductive material.

8. The apparatus of claim 1, wherein the volume is between 50–500 $\mu$l.

9. The apparatus of claim 1, wherein the reaction vessel is round, angular, polygonal, or conical.

10. The apparatus of claim 8 or 9, wherein an outside surface of the reaction vessel is a smooth surface for ensuring maximum heat transfer.

11. The apparatus of claim 1, wherein the liquid aspirating device includes a tube having an overflow portion extending into the body of the reaction vessel for feeding liquid into the cuvette portion.

12. The apparatus of claim 1, wherein the liquid aspirating device includes a tube attached to a side of the body of the reaction vessel for feeding liquid into the cuvette portion.

13. The apparatus of claim 1, 11, or 12, wherein the liquid aspirating device comprises plastic or metal.

14. The apparatus of claim 1, 11, or 12, wherein the liquid aspirating device comprises conductive plastic or non-conductive plastic.

15. The apparatus of claim 13, wherein the reaction vessel with the attached liquid aspirating device is composed of at least one of different conductive or non-conducting plastic materials, composite materials, and combinations of plastic and metal.

16. The apparatus of claim 15, wherein the cuvette portion is at least partially coated with at least one conductive material.

17. The apparatus of claim 14, wherein the reaction vessel with the attached liquid aspirating device is composed of at least one of different conductive or non-conducting plastic materials, composite materials, and combinations of plastic and metal.

18. The apparatus of claim 17, wherein the cuvette portion is at least partially coated with at least one conductive material.

19. A method of taking up, transporting and storing a liquid and for carrying out optical measurements, comprising:

providing an apparatus as claimed in claim 11;

taking up at least one reagent component into the cuvette portion of the reaction vessel by a liquid aspirating device of the apparatus;

providing a sample to be analyzed to the cuvette portion; and performing optical measurements on the sample.

20. The method of claim 19, further including washing the liquid aspirating device following taking up the at least one reagent component.

21. The method of claim 20, wherein the taking up at least one reagent component includes taking up a second reagent component subsequent to washing the liquid aspirating device.

* * * * *

UNITED STATES PATENT AND TRADEMARK OFFICE
CERTIFICATE OF CORRECTION

PATENT NO. : 6,214,626 B1
DATED : April 10, 2001
INVENTOR(S) : Meller et al.

It is certified that error appears in the above-identified patent and that said Letters Patent is hereby corrected as shown below:

Title page,
Item (74), in the "Attorney, Agent, or Firm",
Line 2, "Garret" should read -- Garrett --.

Column 6,
Line 8, "claim 11" should read -- claim 1 --.

Signed and Sealed this

Twenty-eighth Day of August, 2001

Attest:

*Nicholas P. Godici*

NICHOLAS P. GODICI
*Attesting Officer*   *Acting Director of the United States Patent and Trademark Office*